(12) United States Patent
Holmes et al.

(10) Patent No.: US 6,764,856 B2
(45) Date of Patent: Jul. 20, 2004

(54) SEMEN DETECTION SYSTEM AND METHOD

(76) Inventors: Bradley Jay Holmes, 13015 Rotter Rd. East, Alder, WA (US) 98328; Mary Lou Lozon, 13015 Rotter Rd. East, Alder, WA (US) 98328

( * ) Notice: Subject to any disclaimer, the term of this patent is extended or adjusted under 35 U.S.C. 154(b) by 0 days.

(21) Appl. No.: 10/139,088

(22) Filed: May 2, 2002

(65) Prior Publication Data

US 2003/0207459 A1 Nov. 6, 2003

(51) Int. Cl.[7] .............................................. G01N 33/48
(52) U.S. Cl. ..................... 436/86; 436/164; 436/166; 436/168; 436/808; 422/61
(58) Field of Search ............................. 422/56, 58, 61; 436/86, 91, 164, 166, 167, 168, 169, 170, 808

(56) References Cited

U.S. PATENT DOCUMENTS 5,981,206 A * 11/1999 Arter et al. .................... 435/21

OTHER PUBLICATIONS

Criminalistics: An Introduction into Forensic Science, fall 1999, class schedule for Jerome C. Rose, see jcrose@comp.uark.edu.*

* cited by examiner

Primary Examiner—Lyle A. Alexander
(74) Attorney, Agent, or Firm—Black Lowe & Graham PLLC

(57) ABSTRACT

The present invention is directed to a system and method for detecting the presence of semen on material. The system includes a solution of sodium phosphate, maleic acid, dye fast blue salt, naphthyl acid phosphate and deionized water, together with a solution dispenser and absorbent paper. The method for detecting the presence of semen on material using a semen detection solution and absorbent paper includes wetting the suspected semen stain or stain area on the material; blotting the suspected stain or stain area with absorbent paper so as to transfer the moisture from the wetted suspected semen stain or stain area on the material to the absorbent paper; drying the absorbent paper; and applying semen detection solution to the absorbent paper at the location of the transferred suspected stain or stain area.

24 Claims, 2 Drawing Sheets

SEMEN DETECTION SYSTEM AND METHOD

FIELD OF THE INVENTION

This invention relates generally to forensic testing and, more specifically, to a system for creating and resulting compound and associated method for detecting the presence of semen on material.

BACKGROUND OF THE INVENTION

The public has become increasingly consumed with a heightened interest in the prevention of extramarital affairs and unwanted teenage pregnancies. A key to such prevention is the early detection of evidence indicating sexual activity. Historically, interested parties have frequently hired investigators to search for evidence of sexual activity by monitoring the subject. This process can be extremely expensive, and the results inconclusive. Attempts to detect sexual activity based solely on a visual investigation of garments or the activity scene likewise are inconclusive or misleading. There exists a substantial need for a low-cost, easily accessible, reliable and simple system and method that can be used by the general public to detect the presence of semen on material.

SUMMARY OF THE INVENTION

The present invention is directed to a system and method for detecting the presence of semen on material. The system includes a solution of sodium phosphate, maleic acid, dye fast blue salt, naphthyl acid phosphate and water, together with a solution dispenser and absorbent paper. The solution is preferably composed of between about 30% and 50% by weight of sodium phosphate, between about 30% and 50% by weight of maleic acid, between about 1% and 10% by weight of dye fast blue salt, between about 1% and 10% by weight of naphthyl acid phosphate, and up to about 38% by weight of deionized water.

The preferred method for detecting the presence of semen on material using a semen detection solution and absorbent paper consists of wetting the semen stain or suspected stain area on the material; blotting the suspected stain or stain area with absorbent paper so as to transfer the moisture from the wetted semen stain or suspected stain area on the material to the absorbent paper; drying the absorbent paper; and applying semen detection solution to the absorbent paper at the location of the transferred stain or suspected stain area. In the preferred method, if the absorbent paper turns purple within fifteen seconds after application of the semen detection solution, semen is present on the material. On the other hand, if the absorbent paper does not turn purple within fifteen seconds after application of the semen detection solution, semen is not present on the material.

As will be readily appreciated from the foregoing summary, the invention provides a low-cost, easily accessible, reliable and simple system and method that can be used by the general public to detect the presence of semen on materials such as fabrics.

BRIEF DESCRIPTION OF THE DRAWINGS

The preferred and alternative embodiments of the present invention are described in detail below with reference to the following drawings.

DETAILED DESCRIPTION OF THE PREFERRED EMBODIMENT

Figure 1:
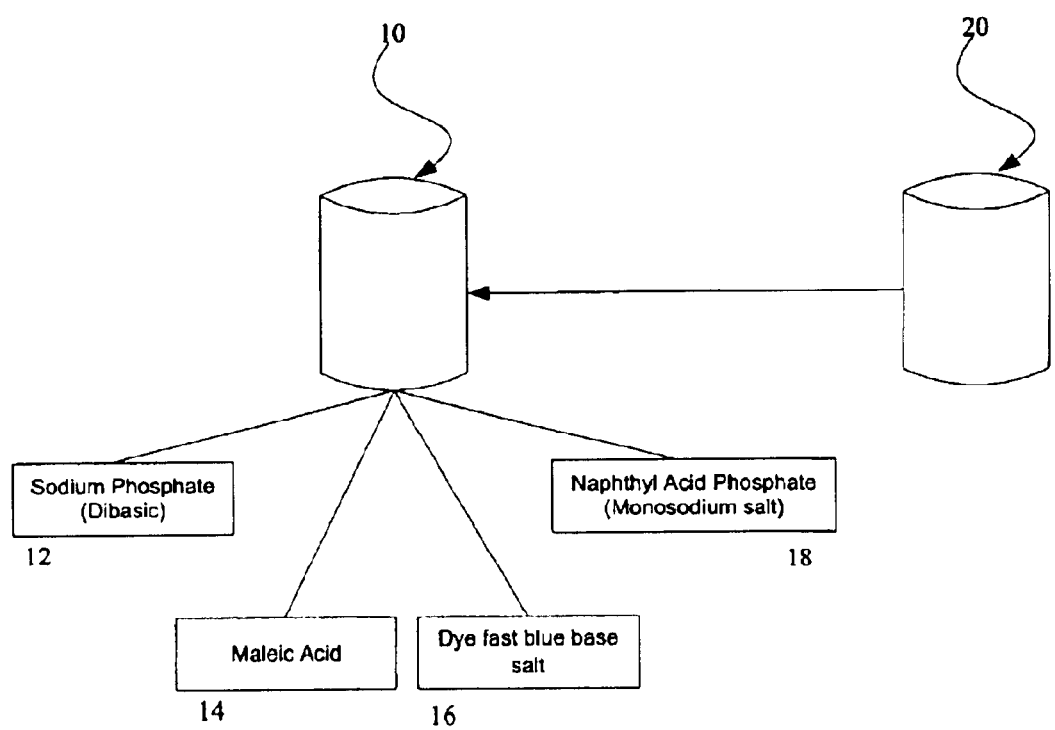
FIG. 1 component view illustrating the composition of a system made in accordance with the present invention.
Figure 1:

The present invention provides a system and method for detecting otherwise invisible traces of dried semen in various materials, such as undergarments. As illustrated with reference to FIG. 1, the system includes ingredients for a dry chemical composition including a combination four different chemicals: sodium phosphate (dibasic) 12; maleic acid 14; dye salt (diazyl dye) 16, preferably dye fast blue salt but optionally any other color of dye salt; and naphthyl acid phosphate (monosodium salt) 18. These four chemicals are combined with water 20, preferably deionized water, to produce a resulting chemical compound 10.

A preferred composition for detecting the presence of semen on material will contain from about 30% to about 50% by weight of sodium phosphate, from about 30% to about 50% by weight of maleic acid, from about 1% to about 10% by weight of dye fast blue salt, from about 1% to about 10% by weight of naphthyl acid phosphate, and up to about 38% by weight of deionized water. In a specific example, the preferred ratios used to produce one ounce of the chemical composition of the present invention requires 12.32 g of sodium phosphate; 12.04 g of maleic acid; 2.24 g dye fast blue salt; and 1.40 g of naphthyl acid phosphate, and 10 ml of deionized water. Variation of these specific ratios within the identified percent weight ranges is contemplated while maintaining the functionality of the resultant compound. Also, the formula can be multiplied in a way that substantially maintains the noted ratios to produce any desired quantity of the compound of the present invention.

In the preferred embodiment, the compound of the present invention is used in conjunction with the other components of the semen detection system, including a 5 ml eyedropper 30 and regular round blotting paper 40. Any type of dispenser may be used in place of the eyedropper 30 of the preferred embodiment. Also, any type of absorbent paper may be used in place of the blotting paper 40.

Figure 2:
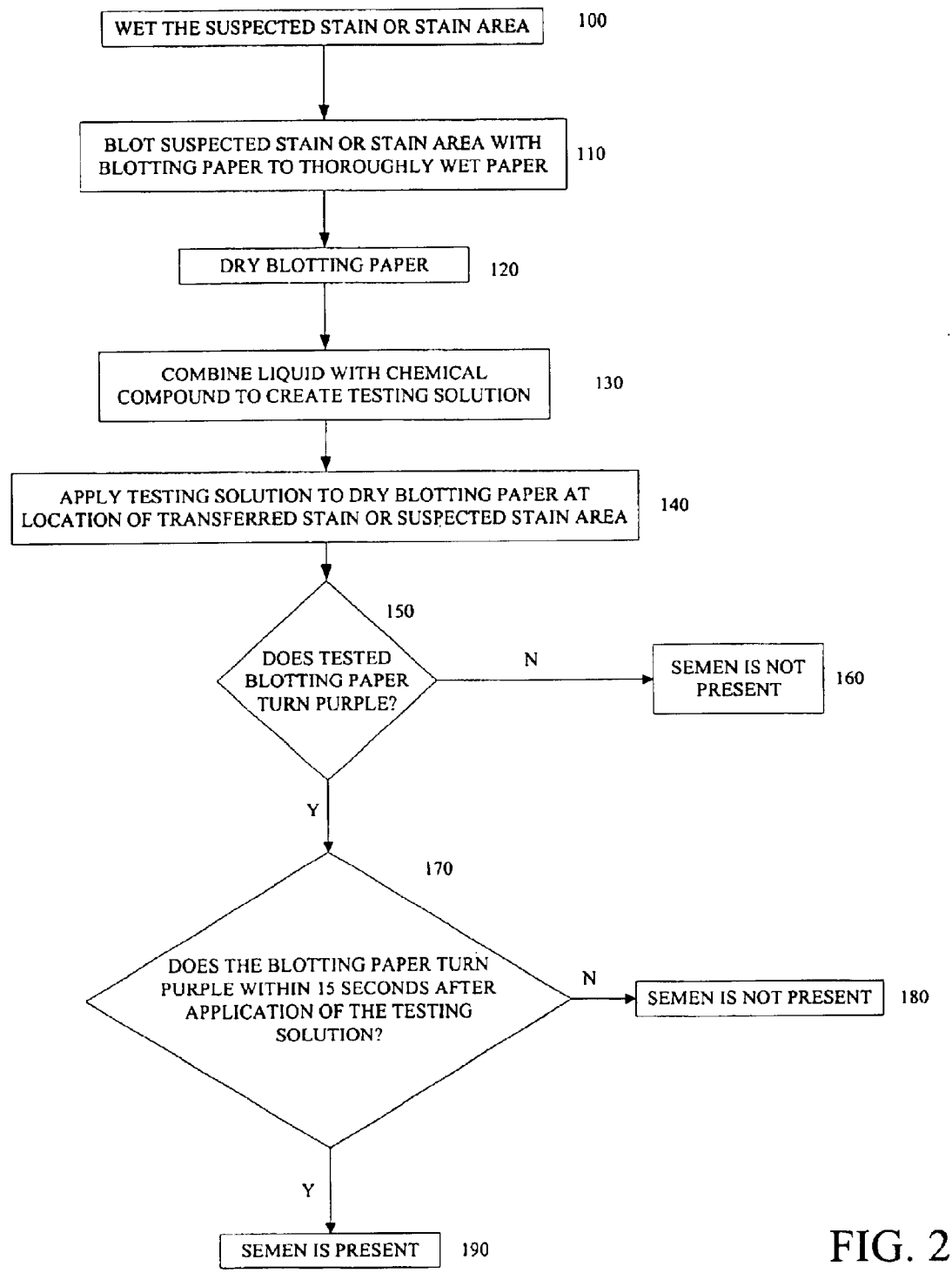
FIG. 2 is a flowchart illustrating the operation of one embodiment of the present invention.

With reference to FIGS. 1 and 2, the operation of the preferred embodiment of the present system of semen detection involves the following steps. At block 100, a user wets the test area of the material with a small amount of the deionized water 20 using the eyedropper 30. If the user can actually see the suspected semen stain, the user wets the specific stain. If the user cannot see the stain, but suspects one may be present, the user wets the suspected stain area. Preferably only one or two drops of the deionized water 20 are used on the test area. The deionized water is allowed to soak into the material fabric.

After the water has soaked into the fabric, but before the wetted fabric has a chance to dry, at block 110, the blotting paper 40 is used to absorb the water from the material. In the preferred embodiment, the user blots the wetted suspected stain or stain area with the blotting paper 40 to thoroughly wet the blotting paper. This is preferably accomplished by pushing down gently on the blotting paper in different places along the test area. If semen is present in the test area, this process transfers the semen from the material being tested to the blotting paper.

In an alternative embodiment, the user wets the blotting paper 40 with the deionized water 20 rather than the material, and rubs the wetted blotting paper on the semen stain or suspected stain area of the material. If semen is present in the test area of the material, this process transfers the semen from the material being tested to the blotting paper.

At block 120, the blotting paper is allowed to dry. Next, at block 130, preferably using the eyedropper 30, approximately 10 ml of the deionized water 20 is mixed thoroughly with the above-described dry chemical composition to produce the chemical compound 10 of the present invention. Any type of container may be used to house the combined mixture of the dry chemical compound and the deionized water. The resulting solution is preferably rigorously mixed (shaken) for at least 30 seconds to ensure complete integration of the dry chemical compound and the deionized water to produce a solution of the chemical compound 10.

At block 140, the resulting solution is added to the previously wetted but now dried blotting paper 40 at the location of the transferred semen stain or suspected stain area. Preferably, one to three drops of the solution are applied to the test location using the eyedropper 30. At decision block 150, the blotting paper 40 that has been tested and to which the solution has been added is examined to determine whether the blotting paper test area has changed to a specific color. In the preferred embodiment, using dye fast blue salt, the specific color to observe is purple. The solution may be manufactured to produce different specific colors indicating a positive test result by altering the type of dye salt. If the blotting paper test area does not turn purple, the logic proceeds to conclusion block 160, which indicates that semen is not present in the suspected stain or stain area. If the blotting paper test area does turn purple, the logic proceeds to decision block 170. At decision block 170, a determination must be made whether the blotting paper test area turns purple within 15 seconds after application of the testing solution. If the blotting paper test area does not turn purple within 15 seconds, the logic proceeds to conclusion block 180, which indicates that semen is not present in the suspected stain or stain area. If the blotting paper test area does turn purple within 15 seconds after application of the testing solution, the logic proceeds to conclusion block 190, which indicates that semen is present. A time piece having a second counter is preferably used to accurately monitor the time between application of the test solution to the blotting paper test area and evaluation of blotting paper coloration.

The system and method of the present invention offers distinct benefits over known systems and methods of semen detection, including ease of use and manufacturing efficiencies. These benefits make the invention useful in a wide variety of settings, including to the home consumer.

While the preferred embodiment of the invention has been illustrated and described, as noted above, changes can be made without departing from the spirit and scope of the invention. For example, a dye salt other than dye fast blue salt may be used to alter the resultant color in the case of positive semen detection. The specific order of performing certain logic blocks 100 through 190 may be changed. For example, combining the deionized water with the dry compound to produce the test solution at block 130 may be performed at a different stage in the testing process, such as at any point prior to applying the testing solution at block 140. Accordingly, the scope of the invention is not limited by the disclosure of the preferred embodiment.

The embodiments of the invention in which an exclusive property or privilege is claimed are defined as follows:

1. A composition of matter indicative of the presence of semen on material, the composition consisting essentially of between about 30% and 50% by weight of sodium phosphate, between about 30% and 50% by weight of maleic acid, between about 1% and 10% by weight of dye salt, between about 1% and 10% by weight of naphthyl acid phosphate, and up to about 38% by weight of water.

2. The composition of claim 1, wherein the solution consists essentially of between about 30% and 35% by weight of sodium phosphate, between about 30% and 35% by weight of maleic acid, between about 5% and 8% by weight of dye fast blue salt, between about 3% and 5% by weight of naphthyl acid phosphate, and between about 17% and 32% by weight of water.

3. The composition of claim 1, wherein the water is deionized water.

4. The composition of claim 1, wherein the dye salt is dye fast blue salt.

5. A system for detecting compounds indicative of the presence of semen on material such as fabric, comprising:
   a solution of sodium phosphate, maleic acid, dye salt, naphthyl acid phosphate and water;
   a solution dispenser; and
   absorbent paper.

6. The system of claim 5, wherein the solution consists essentially of between about 30% and 50% by weight of sodium phosphate, between about 30% and 50% by weight of maleic acid, between about 1% and 10% by weight of dye salt, between about 1% and 10% by weight of naphthyl acid phosphate, and up to about 38% by weight of water.

7. The system of claim 6, wherein the solution consists essentially of between about 30% and 35% by weight of sodium phosphate, between about 30% and 35% by weight of maleic acid, between about 5% and 8% by weight of dye salt, between about 3% and 5% by weight of naphthyl acid phosphate, and between about 17% and 32% by weight of water.

8. The system of claim 5, wherein the water is deionized water.

9. The system of claim 5, wherein the dye salt is dye fast blue salt.

10. A method for detecting compounds indicative of semen on a material, the method comprising:
    wetting an absorbent paper;
    blotting the suspected semen area with the wetted absorbent paper so as to transfer semen on the material to the absorbent paper;
    allowing the absorbent paper to dry;
    applying a solution of sodium phosphate, maleic acid, dye salt, naphthyl acid phosphate and water to the absorbent paper; and if the absorbent paper changes color within a waiting period after application of the solution, concluding that semen might be present on the material.

11. The method of claim 10, further comprising the steps of:
    if the absorbent paper does not change to an expected color within a waiting period after application of the semen detection solution, concluding that semen was not present on the material.

12. The method of claim 10, wherein the semen detection solution consists essentially of between about 30% and 50% by weight of sodium phosphate, between about 30% and 50% by weight of maleic acid, between about 1% and 10% by weight of dye salt, between about 1% and 10% by weight of naphthyl acid phosphate, and up to about 38% by weight of water.

13. The method of claim 12, wherein the step of wetting the suspected semen area on the material is performed using deionized water.

14. The method of claim 12, wherein the dye salt is dye fast blue salt and the expected color is purple.

15. The system of claim 12, wherein the solution consists essentially of between about 30% and 35% by weight of sodium phosphate, between about 30% and 35% by weight of maleic acid, between about 5% and 8% by weight of dye fast blue salt, between about 3% and 5% by weight of naphthyl acid phosphate, and between about 17% and 32% by weight of water.

16. A method for detecting compounds indicative of semen on a material, the method comprising:

wetting a suspected semen area on the material;

blotting the suspected semen area with an absorbent paper so as to transfer moisture from the wetted suspected semen area on the material to the absorbent paper;

allowing the absorbent paper to dry;

applying a solution of sodium phosphate, maleic acid, dye salt, naphthyl acid phosphate and water to the absorbent paper; and if the absorbent paper changes color within a waiting period after application of the solution, concluding that semen might be present on the material.

17. The method of claim 16, further comprising the steps of:

if the absorbent paper does not change to an expected color within a waiting period after application of the semen detection solution, concluding that semen was not present on the material.

18. The method of claim 16, wherein the semen detection solution consists essentially of between about 30% and 50% by weight of sodium phosphate, between about 30% and 50% by weight of maleic acid, between about 1% and 10% by weight of dye salt, between about 1% and 10% by weight of naphthyl acid phosphate, and up to about 38% by weight of water.

19. The method of claim 18, wherein the step of wetting the suspected semen area on the material is performed using deionized water.

20. The method of claim 18, wherein the dye salt is dye fast blue salt and the expected color is purple.

21. The system of claim 18, wherein the solution consists essentially of between about 30% and 35% by weight of sodium phosphate, between about 30% and 35% by weight of maleic acid, between about 5% and 8% by weight of dye fast blue salt, between about 3% and 5% by weight of naphthyl acid phosphate, and between about 17% and 32% by weight of water.

22. A method for detecting the presence of semen on material comprising:

blotting the suspected semen area with absorbent paper so as to transfer semen on the material to the absorbent paper;

drying the absorbent paper;

applying a solution of sodium phosphate, maleic acid, dye salt, naphthyl acid phosphate and water to the absorbent paper at the location of the transferred suspected stain or stain area; and if the absorbent paper changes color within a waiting period after application of the solution, concluding that semen might be present on the material.

23. The method of claim 22, wherein the semen detection solution consists essentially of between about 30% and 50% by weight of sodium phosphate, between about 30% and 50% by weight of maleic acid, between about 1% and 10% by weight of dye fast blue salt, between about 1% and 10% by weight of naphthyl acid phosphate, and up to about 38% by weight of water.

24. The system of claim 23, wherein the solution consists essentially of between about 30% and 35% by weight of sodium phosphate, between about 30% and 35% by weight of maleic acid, between about 5% and 8% by weight of dye fast blue salt, between about 3% and 5% by weight of naphthyl acid phosphate, and between about 17% and 32% by weight of water.

* * * * *